United States Patent
Pera

(10) Patent No.: US 6,772,755 B2
(45) Date of Patent: Aug. 10, 2004

(54) PEN-SHAPED INHALING DEVICE FOR DISPERSING POWDERED MEDICAMENTS THROUGH THE RESPIRATORY TRACT

(76) Inventor: Ivo E. Pera, 1400 St. Charles Pl., Pembroke Pines, FL (US) 33026

( * ) Notice: Subject to any disclaimer, the term of this patent is extended or adjusted under 35 U.S.C. 154(b) by 48 days.

(21) Appl. No.: 10/085,805

(22) Filed: Feb. 28, 2002

(65) Prior Publication Data

US 2002/0121277 A1 Sep. 5, 2002

(51) Int. Cl.[7] .............................................. B65D 83/06
(52) U.S. Cl. ........................ 128/203.15; 128/203.12; 604/58
(58) Field of Search .... 604/58–60; 128/200.14–200.24, 128/203.12, 203.15, 203.23, 207.14

(56) References Cited

U.S. PATENT DOCUMENTS

| | | | |
|---|---|---|---|
| 4,069,819 A | 1/1978 | Valentine et al. | |
| 4,206,758 A | 6/1980 | Hallworth et al. | |
| 4,846,168 A | 7/1989 | Abiko et al. | |
| 5,372,128 A | * 12/1994 | Haber et al. | ............ 128/203.21 |
| 5,881,721 A | * 3/1999 | Bunce et al. | ............ 128/203.21 |
| 6,092,522 A | * 7/2000 | Calvert et al. | ............ 128/203.21 |
| 2001/0020472 A1 | * 9/2001 | Horlin | ............ 128/203.15 |
| 2003/0150454 A1 | * 8/2003 | Burr et al. | ............ 128/203.21 |

FOREIGN PATENT DOCUMENTS

| | | |
|---|---|---|
| EP | 0666085 | 1/1995 |
| GB | 2253200 | 2/1991 |

* cited by examiner

Primary Examiner—Glenn K. Dawson
(74) Attorney, Agent, or Firm—Malin, Haley & DiMaggio, P.A.

(57) ABSTRACT

An inhaler capable of administering powdered medicaments contained in a capsule through the respiratory tract. It's a pen-shaped device formed by a container that preserves the capsules, arranged in vertical parallel lines, and a block having two or more separated elements inside which one capsule is placed in order to be cut or perforated by a cutting element. The powder of the capsule is so released into a chamber with a grid lower surface that keeps the pieces of the case inside and lets only the powder pass through. Once the capsule is placed into its compartment in order to be cut, it will be sufficient to rotate an element on the other ones by means of a support. Then the user places the mouthpiece of the inhaler, separated by the container, into his/her mouth and breathes in, so that the powdered drug dispersed into the chamber can reach the lungs.

33 Claims, 2 Drawing Sheets

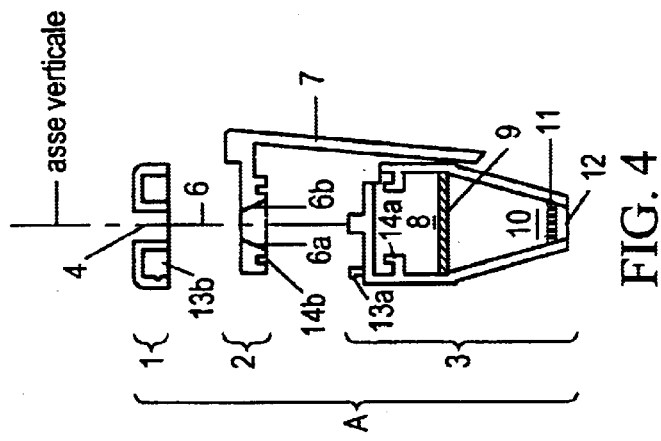
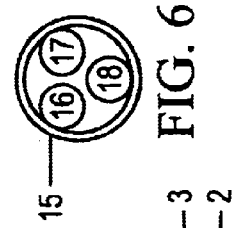
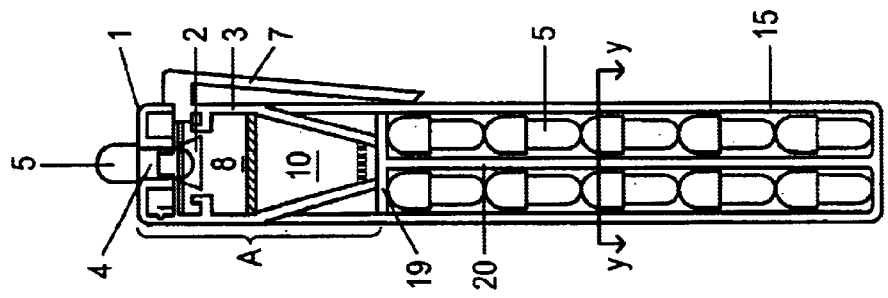
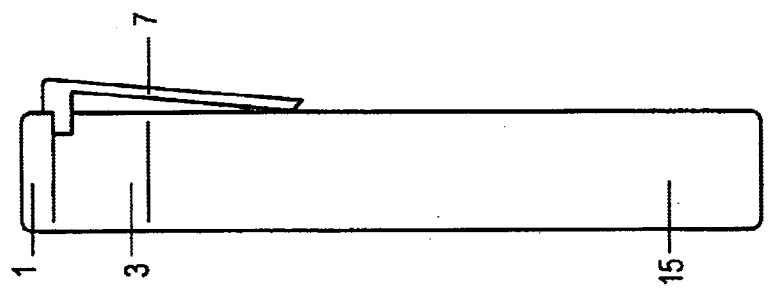
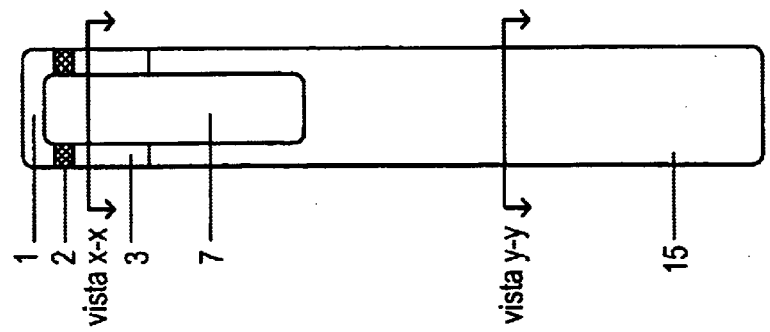

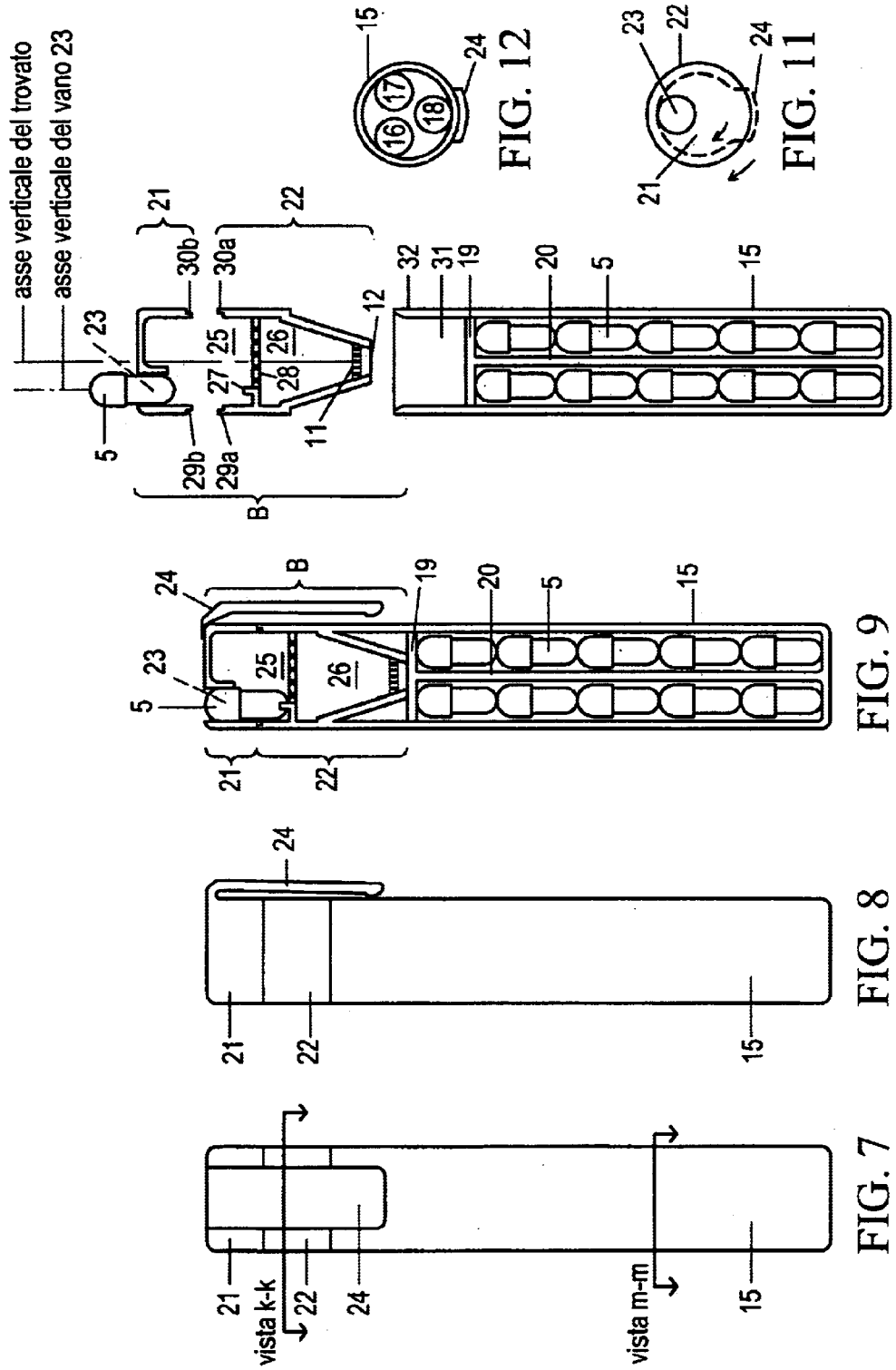

PEN-SHAPED INHALING DEVICE FOR DISPERSING POWDERED MEDICAMENTS THROUGH THE RESPIRATORY TRACT

DESCRIPTION

This application claims the benefit of and priority to European Patent Application No. EP1107678.3, filed Mar. 1, 2001.

TECHNICAL FIELD

The present invention relates to an Inhaling Device capable of administering only one dose of powdered medicaments contained in a capsule at a time, to use in Respiratory Therapy and other Diseases through the topical administration of Medications through the mucous linings of tracheo-bronchial tree and the lungs.

BACKGROUND ART

As the lung is considered to be one of the more effective, noninvasive route of administration to the systemic circulation, a number of powdered medications can be used to treat a variety of conditions that accompany a lot of different diseases. Conditions requiring an inhaler, particularly in such therapy where can be administered to a patient on a program of home care, include: (1) infection, (2) mucous edema, (3) tenacious secretions, (4) foam buildup, (5) bronchosplasms, and (6) loss of compliance.

Many useful medicaments, and especially penicillin and related antibiotics, are subject to substantial or, in some instances, complete alteration by the stomach juices when administered orally. Different patients will react differently to the same dosage at different times. On this account, in past oral dosages was supplemented by checking blood samples to ascertain how much medicament has found its way into the blood stream, or by parental administration. Powdered medicaments administered by inhalation are not frequently used for delivery into the systemic circulation, because of various factors that contribute to erratic or difficult-to-achieve blood levels. Whether or not the powder drugs reaches and is retained in pulmonary alveoli depends critically upon particle size. The literature reports that the optimum particle size for penetration into the pulmonary cavity is of the order of ½ to 7 um.

The general properties given rise to errors of such inhalers in dispensing proper Medicaments are specific directional and velocity characteristics including instability and concentration of the mass of particles administered in a unit volume of air.

Moreover in a definitive clinical setting the patient's inhaling flow can vary significantly. During my research and development I have considered appropriate to test several types of Inhalers with different flow rate in order to develop a novel Inhaling Device, which is obviating the above described disadvantage, by effectively and smoothly inhaling one dose of powdered medicaments at a time into the pulmonary tract by the simple inspiration of air by a patient.

Several devices have been developed for the administration of micronized powders of relatively potent drugs, even if, at present, devices capable of dispersing dry powders contained in a capsule are not known at all. The Norisodrine Sulfate Aerohaler Cartridge (Abbott) is an example of such product. In the use of this Aereohaler, inhalation by the patient causes a small ball to strike a cartridge containing the drug. The force of the ball shakes the proper amount of the powder free, permitting its inhalation. Another device, the Spinhaler (Fisons), TurboHaler from Astra are propeller-driven device designed to deposit a mixture of lactose and micronized cromolyn sodium into the lung, other devices developed by Glaxo, such as Rotahaler, Beclodisk, Diskhaler, Ventodisk and Diskus, all for the administration of powdered drugs for the Respiratory Tract (like Ventolin, Albuterol, Salbritanol, Serevent, etc.) and several other types of these inhalators at present on the market, however most are cumbersome, complicated and expensive.

Clinical practice patients, who are often elderly people, find it difficult to understand the multi-disk method of loading and administering the dry powdered medicament. The illustrative page enclosed with the medicine, though clear, is nevertheless only theoretical. In synthesis everything is seen as complex and difficult and is thus refused. There is the actual possibility that the medicine is not administered because the patient has not noticed that the loader is empty after several doses. Then there are hygienic needs to clean the mechanism with the special brush, etc.

All this frequently results in the premature abandoning of the medicinal formulation, possibly to return to the spray. This, despite its apparent simplicity of use and rapidity, is liable to constant errors, both on the part of the patient and on the part of the nurses, so the spray is almost always delivered on the tongue and not in the lower respiratory tract, leading to repeated doses, with possible cumulative side effects. The serious matter is that the dry powder preparations are almost unknown even in the hospital environment, where the priority in potency and dignity of the "pill" medicine still exists, as it does outside the hospital.

DISCLOSURE OF INVENTION

Furthermore to obviate the above described disadvantages of the Inhalers of the prior art, the inventor developed the present "Pen-shaped Inhaling Device for dispersing powdered medicaments through the respiratory tract", providing the following advantages:

- Easy to use, relieving the patient of mental tension and anxiety regarding the mode of administration and the immediate check of the completed operation.
- Placebo effect advantage for the patient deriving from the psychological tranquillisation due to the simplicity of the method of administration, this being particularly relevant on old age patients.
- Guarantee of the correct dosage and achievement of the therapeutic result, not only to benefit illiterate and elderly patients, but children too.
- Optimum of the dispensing method due to its simplicity, dependability, reliability, fool-proof, and manufacturing low cost.
- Elimination of various Doctors reservations, which currently are not very much in favour to preserve extensively the use of powdered drugs through the use of inhalers.
- Avoiding patient education and extensive training in how to use them, particularly for chronic therapies (many patients have difficulty with inhalers that require more than one step).
- Efficacious and ready to be used with most powdered medicines, just to mention few but not limited to: antibiotics, mucolitics, antioxidants, hormone, vaccines, corticosteroids, etc., which are still not prescribed via inhalations due to lack of efficient devices and cultural instruction.

Elimination of the confusion between long-acting and ready-to-use medicines.

Resolution of the problem of patient co-operation.

Eye appealing and very small.

Moreover, the Inhaling Device in question eliminates manual problems, problems of maintenance, hygiene, comprehension, mistaken use and psychological conditions, and there is no doubt that the Inhaling Device of the present invention is the most uncomplicated and efficient method available for delivery powdered medicaments via the respiratory tract.

On the basis of what is stated, considering that the Inhaling Device is specifically dedicated to clinical use in the administration of powdered medicines which carry out their action locally on the respiratory tract or through the lung as noninvasive route of administration to the systemic circulation, it is held that this mechanism is capable of eliminating difficulties and uncertainty due to current methods of administration.

The elimination of the obstacles that compromise the use of a decisive weapon such as the one object of this invention is thus desirable. The development of the Inhaling Device proposed is needful, to properly dispense powered medicines, and for other similarly interesting applications with potentially enormous developments which can be hypothesized for other substances such as:

Agents useful for calcium regulation (e.g., calcitonin, parathyroid hormone, and the like):

Analgesic/antipyretics (e.g., aspirin, acetaminophen, ibuprofen, naproxen sodium, buprenorphine hydrochloride, propoxyphene hydrochloride, propoxyphene napsylate meperidine hydrochloride, hydromorphone hydrochloride, morphine sulfate, oxycodone hydrochloride, codeine phosphate, dihydrocodeine bitartrate, pentazocine hydrochloride, hydrocodone bitartrate, levorphanol tartrate, diflunisal, trolamine salicylate, nalburphine hydrochloride, mefenamic acid, butorphanol tartate, choline salicylate, butalbital, phenyltoloxamine citrate, diphenhydramine citrate, methotrimeprazine, cinnamedrine hydrochloride, meprobamate, and the like);

Antianginal agents (e.g., beta-adrenergic blockers, calcium channel blockers (e.g., nifedipine, diltiazem hydrochloride, and the like), nitrate (e.g., nitroglycerin, isosorbide dinitrate, pentaerythritol tetranitrate, erythrityl tetranitrate, and the like);

Antidepressant (e.g., doxepin hydrochloride, amoxapine, trazodone hydrochloride, amitriptyline hydrochloride, maprotiline hydrochloride, phenelzine sulfate, desipramine hydrochloride, nortriptyline hydrochloride, tranylcypromine sulfate, fluoxetine hydrochloride, imipramine hydrochloride, imipramine pamoate, nortriptyline, amitriptyline hydrochloride, isocarboxazid, desipramine hydrochloride, trimipramine maleate, protriptyline hydrochloride, and the like);

Antianxiety agents (e.g., lorazepam, buspirone hydrochloride, prazepam, chlordiazepoxide hydrochloride, oxazepam, chlorazepate dipotassium, diazepam, hydroxyzine pamoate, hydroxyzine hydrochloride, alprazolam, droperidol, halazepam, chlormezanone, and the like);

Antiharrythmics (e.g., bretylium tosylate, esmolol hydrochloride, verapamil hydrochloride, amiodarone, encainide hydrochloride, digoxin, digitoxin, mexiletine hydrochloride, disopyramide phosphate, procainamide hydrochloride, quinidine sulfate, quinidine gluconate, quinidine polygalacturonate, flecainide acetate, tocainide hydrochloride, lidocaine hydrochloride, and the like);

Antiarthritic agents (e.g., phenylbutazone, sulindac, penicillamine, salsalate, piroxicam, azathioprine indomethacin, meclofenamate sodium, gold sodium thiomalate, ketoprofen, auranofin, aurothioglucose, tolmetin sodium and the like);

Antibacterial agents (e.g., amikacin sulfate, aztreonam, chloroamphenicol, chloramphenicol palmitate, chloamphenicol sodium succinate, cirpofloxacin hydrochloride, clindamycin hydrochloride, clindamycin palmitate, clindamycin phosphate, metronidazole, metronidazole hydrochloride, gentamicin sulfate, licomycin hydrochloride, tobramycin sulfate, vancomycin hydrochloride, polymyxin B sulfate, colistimethate sodium, colistin sulfate and the like);

Anticoagulants (e.g., heparin, heparin sodium, warfarin sodium, and the like);

Anticonvulsants (e.g., valproic acid, divalproate sodium, phenytoin, phenytoin sodium, clonazepan, primidone, phenobarbitol, phenobarbitol sodium, carbamazepine, amobarbital sodium, methsuximide, metharbital, mephobarbital, mephenytoin, phensuximide, paramethadione, ethotoin, phenacemide, secobarbitol sodium, clorazepate dipotassium, trimethadione, and the like);

Antidepressant (e.g. doxepin hydrochloride, amoxapine, trazodone hydrochloride, amitriptyline hydrochloride, maprotiline hydrochloride, phenelzine sulfate, desipramine hydrochloride, nortriptyline hydrochloride, tranylcypromine sulfate, fluxetine hydrochloride, doxepin hydrochloride, imipramine hydrochloride, imipramine pamoate, nortriptyline, amitriptyline hydrochloride, isosarboxazid, desipramine hydrochloride, trimipramine maleate, protriptyline hydrochloride, and the like);

Antifibrinolytic agents (e.g., aminocaproic acid);

Antifungal agents (e.g., griseofulcin, keloconazole, and the like);

Antigout agents (i.e., colchicine, a'iopurinol and the like);

Antihypertensive agents (e.g., trimethaphan camsylate, phenoxybenzamine hydrochloride, pargyline hydrochloride, desertpidine, diazoxide, guanethidine monosulfate, minoxidil, rescinnamine, sodium nitroprusside, rauwolfia serpentina, alseroxylon, phentolamine mesylate, reserpine, and the like);

Anti-infectives (e.g., GM-CSF);

Antimanic agents (i.e., lithium carbonate);

Antimicrobials (e.g., cephalosporins (e.g., cefazolin sodium, cephradine, cefaclor, cephapirin sodium, ceftisoxime sodium, cefoperazone sodium, cefotetan disodium, cefutoxime azotil, cefotaxime sodium, cefadroxxil monohydrate, ceftazidime, cephalexin, cephalothin sodium, cephalexin hydrochloride monohydrate, cefamandole nafate, cefoxitin sodium, cefonicid sodium, ceforanide, ceftriaxone sodium, ceftazidime, cefadroxil, cephradine, cefuroxime sodium, ceforanide, ceftraxone sodium, ceftazidime, cefadroxil, cephradine, cefuroxime sodium and the like), penicillins (e.g., ampicillin, amoxicillin, penicillin G benzathine, cyclacillin, ampicillin sodium, penicillin G potassium, penicillin V potassium, piperacillin sodium, oxacillin sodium, bacampicillin hydrochloride, cloxacillin sodium, ticarcillin disodium, azlocillin sodium, carbenicillin indanyl sodium, pinicillin G potassium, penicillin G procaince, methicillin sodium, nafcillin sodium, and the like), erythromycins (e.g. erythromycin ethylsuccinate, erythromycin, erythromicin estolate, erythromycin lactobionate, erythromicin siearate, erythromicin ethylsuccinate, and the like) tetracycline (e.g., tetracycline hydrochloride, doxycycline hyclate, minocycline hydrochloride, and the like), and the like);

Antimigraine agents (e.g., erotamine tartrate, propanolol hydrochloride, isomeheptene mucate, dichloralphenazone, and the like);

Antinauseant/antiemetics (e.g., meclizine hydrochloride, nabilone, prochlor-perazine, dimenhydrinate, promethazine hydrochloride, thiethylperazine, scopolamine, and the like);

Anti-oxidants (e.g., beta-carotene, butylated hydroxynisole, butylated hydroxy-toluene, catalases, coenzyme Q10, glutathione, copper sebacate, folic acid, manganese, retinol, pycnogenol, selenium, superoxide dismutase, lycopene, lipoic acid, acetyl-1-carnitine, N-acetyl cysteine, linoleic acid, vitamins A, B2, B6, B12, C and E, taurine, zinc, adenosine, allicin, aloe, alpha lipoic acid, BHA, BHT, bilirubin, capsaicin, catechin, cysteine, coumarin, curcumin, dimethylglycine, glycine, ferrous fumarate, genistein, ginger, ginkgo biloba, gallates, gluconate, green tea, isoascorbic acid, L-glutamine, L-methyl methionine, L-seleno cysteine, L-seleno methionine, lutein, melatonin, methionine reductase w(Cu—Zn or Mn), N-acyl 1-cysteine esters, N-acyl 1-methionine esters, poplar bud, procyanidin, pycnogenol, resveratrol, rosmary, rutin, rutinose, selenium-yeast, seleno cysteine, seleno methionine, silybum marianum, sodium bisulfite, sodium metasulfite, sodium sulfite, sodium thiosulfite, spirulina, sulfuraphane, superoxide dismutase (SOD), taurine, thioglycerol, thiol, thiosorbitol, thiourea, wheat grass, zinc gluconate and the like);

Antiparkinson agents (e.g., ethosuximide, and the like);

Antiplatelet agents (e.g., aspirin, empirin, ascriptin, and the like);

Antistamine/antipruritics (e.g., hydroxyzine hydrochloride, diphenhydramine hydrochloride, chlorpheniramine maleate, brompheniramine maleate, cyproheptadine hydrochloride, terfenadine, clemastine fumarate, triprolidine hydrochloride, carbinoxamine maleate, diphenylpyraline hydrochloride, phenindamine tartrate, azatadine maleate, tripelennamine hydrochloride, dexchlorpheniramine maleate, methdilazine hydrochloride, trimprazine tartrate, and the like);

Antipsychotic agents (e.g., haloperidol, loxapine succinate, loxapine hydroxhloride, thioridazine, thioridazine hydrochloride, thiothixene, fluphenazine hydrochloride, fluphenazine decanoate, fluphenazine enanthate, trifluoperazine hydrochloride, chlorpromazine hydrochloride, perphenazine, lithium citrate, prochlorperazine, and the like);

Antiulcer/antireflux agents (e.g., famotidine, cimetidine, ratitidine hydrochloride, and the like);

Antiviral agents (e.g., interferon gamma, zidovudine, amantadine hydrochloride, ribavirin, acyclovir, and the like);

Bronchiodialators (e.g., sympathomimetics (e.g., epinephrine hydrochloride, metaproterenol sulfate, terbutaline sulfate, isoetharine, isoetharine mesylate, isoetharine hydrochloride, albuterol sulfate, albuterol, bitolterol, mesylate isoproterenol hydrochloride, terbutaline sulfate, epinephrine bitartrate, metaproterenol sulfate, epinephrine, epinephrine bitartrate), anticholinergic agents (e.g., ipratropium bromide), xanthines (e.g. aminophylline, dyphylline, metaproterenol sulfate, aminophylline), mast cell stabilizers (e.g., cromolyn sodium), inhalant cortisteroids (e.g., flurisolide-beclomethasone dipropionate, beclomethasone dipropionate monohydrate), salbutamol, beclomethasone dipropionate monohydrate), salbutamol, beclomethasone dipropionate (BDP), ipratropium bromide, budesonide, ketotifen, salmeterol, xinafoate, terbutaline sulfate, triamcinolone, theophylline, nedocromil sodium, metaproterenol sulfate, albuterol, flunisolide, and the like);

Hemorheologic agents (e.g., pentoxifylline);

Hypoglycemic agents (e.g., human insulin, purified beef insulin, purified pork insulin, glyburide, chlorpropamide, glipizide, totalbutamide, tolazamide, and the like);

Hypolipidemic agents (e.g. clofibrate, dextrothyroxine sodium, probucol, lovastatin, niacin, and the like);

Hormones (e.g., androgens (e.g., danazol, testosterone cypionate, fluoxymesterone, ethyltostosterone, testosterone enanihate, methyltesterone, fluoxymesterone, testosterone cypionate), estrogens (e.g., estradiol, estropipate, conjugated estrogens), progestins (e.g.methoxyprogesterone acetate, norethindrone acetate), cortisteroids (e.g. triamcinolone, betamethasone, betamethasone sodium phosphate, dexamethasone, dexamethasone sodium phosphate, dexamethasone acetate, prednisone, methylprednosolone acetate suspension, triamcinolone acetonide, methylprednisolone, prednisolone sodium phosphate methylprednisolone sodium succinate, hydrocortisone sodium succinate, methylprednisolone sodium succinate, triamcinolone hexacatonide, hydrocortisone, hydrocortisone cypionate, prednisolone, fluorocortisone acetate, paramethasone acetate, prednisolone tebulate, prednisolone acetate, prednisolone sodium phosphate, hydrocortisone sodium succinate, and the like), thyroid hormones (e.g., levothyroxine sodium) and the like;

Nucleic acids (e.g., sense or anti-nucleic acids encoding any protein suitable for delivery by inhalation, including the proteins described herein, and the like);

Proteins (e.g., DNase, alginase, superoxide dismutase, lipase, and the like);

Sedatives/hypnotic (e.g., ergotamine tartrate, propanol hydrochloride, isomeheptene mucate, dichloralphenazone, and the like);

Thrombolytic agents (e.g., urokinase, streptokinase, altoplase, and the like).

Additional agents contemplated for delivery employing the invention inhalation device and methods described herein include agents useful for the treatment of diabetes (e.g., activin, glucamon, insulin, somatostatin, proinsulin, amylin, and the like), carcinomas (e.g., taxol, interleukin-1, interleukin-2, (especially useful for treatment of renal carcinoma), and the like, as well as leuprolide acetate, LHRH analogs (such as nafarelin acetate), and the like, which are especially useful for the treatment of prostatic carcinoma), endometriosis (e.g., LHRH analogs), uterine contraction (e.g., oxytocin), diuresis (e.g., vasopressin), cystic fibrosis (e.g., Dnase (i.e., deoxyribonuclease), SLPI, and the like), neutropenia (e.g., GCSF), lung cancer (e.g., beta 1-interferon), respiratory disorders (e.g. superoxide dismutase), RDS (e.g., surfactants, optionally including apoproteins), and the like.

Presently preferred indications which can be treated employing the invention inhalation device and methods described herein include diabetes, carcinomas (e.g., prostatic carcinomas), bone disease (via calcium regulation), cystic fibrosis and breathing disorders (employing bronchodilators), and the like.

Accordingly, there exists a definite need for a tiny dry powder pharmaceutical delivery device that can use many different powdered pharmaceuticals, which can safely stored to maintain stability until dispensing, without any loss of uptake efficiency due to its advanced design, or to excessive absorption within the mouth or throat. The present invention satisfies this need and provides further related advantages.

The clinical, pharmacological, economic and finally the social advantages can be anticipated together with the co-operation of the patient (it is sufficient to consider the reduction of anxiety due to the easiness to use the device, the fact that the patient no longer needs the assistance of members of the family, with the reduction of injections, and with lower hospitalization required, etc.).

The interest compliance and serenity of the patient is favoured (many speak of anxiety in complex manoeuvres) where he is called to execute the minimum number of actions possible and with a strong temporal and material connotation, i.e. with a precise identification of the act performed in the same way as the taking of any pill, with the result of the exact perception of the completed event (let us not forget that the patient often doubts that he has correctly administered the medicine via aerosol). Consequently there is a strong concentration of faith in the act itself, which as well as scientific becomes "magical", therefore saving and above all worthy of faithfulness.

The regular imposition of the right doses is not the least of the advantages of the methodologies in question. The possibility of lower production costs and the better perception of results by the prescribing doctor, and hence the increase of confidence in the medicinal formulation, is another advantage of the methodology that cannot be ignored.

The use of the breath-activated inhaler of the present invention is extremely simple, fool-proof, and the user will easily achieve maximum control of his health, instead the more complicated models available on the market, anyone using them will be given extensive training for its use. Nevertheless it is generally estimated that with the standard inhaler only about ten percent (10%) of the inhaler drug actually reaches the lungs, the remaining ninety percent (90%) is deposited on the lining of the mouth and throat, and when relief is not forthcoming, the inhaler use tends to quick press for another dose of the drug. Using such inhalers to often is likely, under certain circumstances to have serious unpleasant side effects, such as mild irritation in the throat, dysphonia, nausea, jitteriness, indigestion, gastric reflux, insomnia, thrush, hoarseness, coughing, oropharyngeal candidasis, etc.

The use of the Inhaler proposed by the present invention through the respiratory tract may provide an efficient means of administering dry powder medicaments such as vasoconstrictors, antihistaminics, antispamodics, antipeptics, antibronchiolitis, B2-stimulants-corticosteroids, antivirals, antifungals, antioxidants, antileukotrienes, antiallergens, antibiotics, human proteins, peptides, etc., which will generally requires a smaller dosage than would be necessary if the drug were given systematically, infection is often accompanied by one or more of the five other conditions cited above.

The principal purpose of the present invention is to provide an Inhaling Device for dispensing only one dose of powdered medicaments at a time into the Respiratory Tract and is intended to be easy to use, inexpensive and possibly used more times.

The present invention relates to an Inhaling Device suitable for delivery, via the respiratory tract, therapeutic medication and includes among its objects and advantages increased convenience in medication with dry medicaments in powder form, especially with respect to accuracy of dosage and accurate placement of the drug.

The inhaler object of this invention is useful also with antibiotics, steroids and other difficulty soluble compounds. Problems associated with the formulation of this drug include aggregation, caking, particle-size growth and often clogging, which using the present Inhaler is completely avoided.

It has been discovered that the use of the Inhaler of the present invention for dispensing powdered medicaments available in the form of fine powders, can be practiced to cause effective therapeutic effect. It is also possible to combine the general treatment thus resulting with high local concentration of the same medicament in the respiratory tract.

Solid inhalation therapy is of value in connection with many therapeutic agents, including antiseptic bronchiolytics, and vaso-constrictors, and is indicated for at least some of the known anti-histamine drugs.

Many therapeutic agents that are water-soluble will be found effective by solid inhalation, by both the effect and the degree of effectiveness need to be established by specific test in connection with each substance.

Many ingredients can be added as Membrane Permeation Inhaler to the Drug formulations to increase their barrier permeability, but the preferred one and most effective is lactose.

Accordingly, the present invention will succeed in obtaining such constancy by providing a device that is to be utilized by the patient by breathing in, in a simple, substantially normal way. Utilized the energy of the air flowing through the device to deliver into the lining a single dose of powdered medicaments at a time, which charge is delivered quickly, shortly after inhalation begins, and finds its way to its resting place. Thus the device itself and the body passages first receiving the stream of air are thoroughly swept and scavenged with pure air during a major portion of the breathing-in process. I have found that administration in this way not only contributes to deep penetration of the medicament, but that it becomes unnecessary to pulverize or micronize the medicament into a true smoke. The use of larger particle tends to increase the reliability with which a uniform fraction of the material will pass on through the body passages first receiving the stream without getting caught on the moist walls.

With the Inhaler proposed by the present invention the absorption is virtually as rapid as the drug can be delivered into the alveoli of the lungs, since the alveolar and vascular epithelial membranes are quite permeable, blood flow is abundant, and there is a very large surface for absorption.

It is an object of this invention to provide an extremely simple device which is sturdy, dependable, reliable, fool-proof and which will maintain its characteristics for a long period so that if a considerable time about elapse between the original manufacture of the item and its utilization, the therapeutic efficacy of the drug will remain comparatively undiminished.

This invention makes possible to dispense any type of powdered drugs that are at all times completely under the control of the user. It will thus be seen that the invention provides a simple and convenient means of dispensing powdered drugs, and it is capable of extremely wide applications.

The Inhaling Device of this invention can be manufactured quite easily using means of injection mouldings well known in the art, thereby affecting substantial cost reduction in manufacturing the device without adversely affecting the medicament administration inhalation.

With this and other objects in view the invention consists in the details of an inexpensive but efficient inhalator, convenient and easy to use and of low cost to the user so that the device may be discarded following the single administration of the contained medicament.

As can you see from the drawings included, the concept in question is carried out through the use of administration devices which can be adapted in their dimensions, external aspect and internal and external conformation: however, all the devices follow the logic of a single and exact dose of medicine in a container made of plastic, or other appropriate material which can also be biodegradable, and suitable for inhalation, thanks to its conformation.

An Inhaling Device for dispersing powdered medicaments through the respiratory tract, according to the invention, comprises:

means to preserve the capsules in order to be easily and conveniently carried and used, with a container (15) harmoniously integrated in the whole device;

means to hold a capsule and allow the powdered drug it contains to come out, by an assembly of two or more separated elements that constitute a single block (A) or (B);

means to hold the capsule inside said block, by a compartment into which the capsule is placed and is held still during the operation of incision, so as to guarantee the dispersion of the powdered drug into a chamber of said block;

means to split the capsule, by a cutting element preferably formed by a point, a blade, a cutting surface, or any other cutting element capable of perforating or cutting the capsule, according to one of the two possible embodiments of this device;

means to rotate one of the elements on the other elements forming the block of the inhaler, in order to cause the powdered drug completely come out from the capsule, after the cut or incision of the case of the same capsule, with a support by means of which it's possible to rotate one element on the other ones;

means to hold the pieces of the case of the capsule, after it has been split, and to prevent the powder from aggregating, by a chamber with a grid lower surface that keeps the bigger pieces of the drug not completely pulverized, as well as the pieces of the case of the capsule, while letting the powdered drug pass through;

means to deliver the powder of the capsule released into the lower part of the block of the inhaler, by a mouthpiece from which the user can directly inhale the powder;

means to prevent the powder from aggregating, by a porous filter placed near the mouthpiece of the inhaler.

The inhaler object of this invention can be used in a first embodiment wherein, with reference to FIGS. 1, 2, 3, 4, 5 and 6, the capsule is cut by means of a rough surface touching it. This system comprises:

means to preserve the capsules (5) in order to be easily and conveniently carried and used, with a container (15) harmoniously integrated in the whole device, inside which the capsules (5) are arranged in three vertical parallel lines (16) (17) and (18);

means to hold a capsule (5) inside the block (A), by an element (1) comprising an open compartment (4), into which the capsule (5) is placed, with its side walls touching the perimeter of said compartment (4);

means to cut the capsule (5), by an element (2) comprising a half-conical opening (6), with the vertex upwards and with rough internal side surfaces (6a, 6b) that facilitate the operation of incision of the lower part of the case of the capsule (5), following the rotation of the element (2) on the other elements (1) and (3) of block (A);

means to release the powdered drug inside the block (A), immediately after the case of the capsule (5) has been split, by an element (3) formed by two chambers (8) and (10), divided one from the other by a grid (9);

means to rotate the element (2) on the elements (1) and (3) forming the block (A), by a long rectangular support (7) connected to the element (2);

means to fit the element (1) to the element (3) of block (A), by three equal components placed at the vertexes of an equilateral triangle inscribed in the circular section of the upper part of the element (3) of block (A); each of them is formed by a small wing (13a), placed in horizontal position and belonging to the element (3), which perfectly fits inside the notch (13b) of the element (1);

means to fit the element (2) to the element (3) of block (A), by two equal components; each of them is formed by a small wing (14a), placed in vertical position and belonging to the element (3), which perfectly fits inside the groove (14b) of the element (2);

means to hold the pieces of the case of the capsule (5), after it has been split, and to prevent the powder from aggregating, by a chamber (8) with a grid lower surface (9) having a series of slots that keep the bigger pieces of the drug not completely pulverized, as well as the pieces of the case of the capsule (5), while letting the powdered drug pass through;

means to deliver the powder of the capsule (5) released into the chamber (10), by a mouthpiece (12) from which the user can directly inhale the powder.

means to prevent the powder from aggregating, by a porous filter (11) placed near the mouthpiece (12) of the inhaler.

The inhaler can be used in a second embodiment wherein, with reference to FIGS. 7, 8, 9, 10, 11 and 12, the capsule is cut by splitting its case with a cutting element. This system comprises:

means to preserve the capsules (5) in order to be easily and conveniently carried and used, with a container (15) harmoniously integrated in the whole device, inside which the capsules (5) are arranged in three vertical parallel lines (16) (17) and (18);

means to hold a capsule (5) inside the block (B), by an element (21) comprising an open compartment (23), into which the capsule (5) is placed, with its side walls touching the perimeter of said compartment (23);

means to split the capsule (5), by a cutting element (27), consisting of a rectangular pointed blade; when the capsule (5) is placed into the compartment (23), the lower part of its case will be cut for incision by the cutting element (27);

means to release the powdered drug inside the block (B), after the split of the capsule (5), by an element formed by two chambers (25) and (26), divided one from the other by a grid (28);

means to rotate the cover (21) on the element (22) of block (B), in order to cause the cutting element (27) split the case of the capsule (5) and let the powdered drug completely come out, by a long rectangular support (24) connected to the cover (21);

means to fit the cover (21) to the element (22) of block (B), by a circular groove along the entire perimeter of the base of the cover (21) and of the upper end of the element (22); with reference to the drawing of FIG. 10, it's possible to identify the tracks (29a) and (30a) of the groove on the internal upper part of the element (22), that perfectly fit into the tracks (29b) and (30b) of the groove on the external lower part of the cover (21);

means to hold the pieces of the case of the capsule (5), after it has been split, and to prevent the powder from aggregating, by a chamber (25) with a grid lower surface (28) having a series of slots that keep the bigger pieces of the drug not completely pulverized, as well as the pieces of the case of the capsule (5), while letting the powdered drug pass through;

means to deliver the powder of the capsule (5) released into the chamber (26), by a mouthpiece (12) from which the user can directly inhale the powder.

means to prevent the powder from aggregating, by a porous filter (11) placed near the mouthpiece (12) of the inhaler.

This device has such a size that allows it to be conveniently and easily carried in a handbag or even in your pocket.

In addition, this device has such a shape that the complete assembly of its elements is virtually similar to the conformation of a normal cylindrical pen or pencil, with the vertical dimension greater than the other two, however comparable with the dimensions of a normal pen.

This device is made of plastic material and may be externally coloured as desired, in order to make it anonymous, so that it can normally go unobserved.

This device has a very low weight that increases its convenient and easy use or transport, since it has a plastic structure made of thin walls and it has a series of empty spaces inside.

The external support (7) or (24), according to the embodiment of the device to which we refer, facilitates the convenient transport of the inhaler (for example in the pocket of your shirt) thanks to its clip.

Conveniently, this device can reduce to the minimum the operations that must be performed for the inhalation of the powdered drug by the user; in particular, the shape and the position of the various chambers of the device allow the user to perform the operation of incision of the capsule (5) and the consequent inhalation of the powdered drug, by simple operations that do not require a particular predisposition to the use of inhalers like this.

Advantageously, the container (15) inside which the capsules (5) are placed in order to be preserved until the moment of their use, guarantees the greatest hygiene of the capsules (5), protecting them from the dust or from contact with other external agents.

The container (15) can house a number of capsules (5) that is sufficient to guarantee their use for several administrations; in particular, the proposed embodiments of the invention provide a container (15) capable of holding three vertical parallel lines (16) (17) and (18), each one containing five capsules (5), for a total of fifteen capsules (5).

However, this invention can provide containers (15) capable of holding a different number of capsules (5), particularly considering the advantages of a smaller device, in the case the container holds a minor number of capsules (5).

This device may be used more times and, in order to ensure the greatest hygiene, the mouthpiece (12) from which the user inhales the powdered drug that is come out from the capsule (5), is held and protected by the upper part of the container (15), so that, when the inhaler is not used, the maximum protection from the dust and, in general, from external agents will be guaranteed.

The compartment (4) or (23), into which the capsule (5) is placed in order to be cut, has such a size that permits the complete insertion of the capsule (5) inside it, ensuring a greater stability of the same capsule (5) during the operation of its incision, and preventing it from accidentally escaping from said compartment (4) or (23).

The powder released on the base of the device is inhaled by the user, placing directly the mouthpiece (12) into his/her mouth and breathing in, so that the powdered drug coming out from the mouthpiece (12) enters the mouth and reaches the lungs.

With reference to the embodiment of the device depicted in FIGS. 1, 2, 3, 4, 5 and 6, the body of the inhaler is essentially formed by two parts that can be assembled each other: the block (A) and the container (15), inside which the capsules (5) are preserved until the moment of their use. The block (A), in its turn, is essentially formed by three parts that can be assembled each other: the cover (1) and the elements (2) and (3). Such a conformation facilitates the manufacturing and assembling of the inhaler, considerably reducing the costs of the mass production. With reference to FIGS. 1, 2, 3, 4, 5 and 6, the capsule (5) is cut by rubbing the lower part of its case over the rough surface of the half-conical opening (6), whose internal surfaces (6a, 6b) are made of such a material that chafes the case of the capsule (5), following the rotation of the element (2) by means of the support (7) connected to the same element (2).

With reference to FIGS. 1, 2, 3, 4, 5 and 6, the operation of incision of the capsule (5) and the consequent inhalation of the powdered drug by the user, can be easily performed following these operations: it's sufficient to keep the block (A) of the inhaler with one hand and, once the capsule (5) has been placed in the compartment (4) of the cover (1), with the thumb of the other hand you'll rotate the element (2) on the other elements (1) and (3) forming block (A), by means of the support (7), so as to split the case of the capsule (5); then you place the device into your mouth and inhale the powdered drug.

With reference to FIGS. 1, 2, 3, 4, 5 and 6, the internal walls (6a) and (6b) of the half-conical opening (6) included in the element (2) of block (A), are made of a material composed of a paste of plastic and vitreous material, which makes said surfaces sufficiently rough to guarantee the incision of the case of the capsule (5) following the rubbing.

With reference to FIGS. 1, 2, 3, 4, 5 and 6, such material forming the internal rough surfaces of the opening (6) is also sufficiently stiff, so as to prevent their crumbling or any pulverization of their external layer.

With reference to FIGS. 1, 2, 3, 4, 5 and 6, in order to ensure a greater dispersion of the powdered drug into the chamber (10), this takes such a conformation that the half-conical shape, with the vertex downwards, facilitates the outflow of the powder towards the mouthpiece (12) so that it can be easily and conveniently inhaled by the user.

With reference to FIGS. 1, 2, 3, 4, 5 and 6, under the compartment (4) where the capsule (5) is placed in order to be cut, there is a chamber (8), with a grid lower surface (9) having a series of slots, which allows the pieces of the case of the capsule (5) to remain inside the chamber (8). Said grid (9) has the important function to prevent the powder from aggregating in a humid atmosphere, obstructing in this way its dispersion into the next chamber (10) and the consequent inhalation by the user.

With reference to the embodiment of the device depicted in FIGS. 7, 8, 9, 10, 11 and 12, the body of the inhaler is essentially formed by two parts that can be assembled each other: the block (B) and the container (15), inside which the capsules (5) are preserved until the moment of their use. The block (B), in its turn, is essentially formed by two parts that can be assembled each other: the cover (21) and the element (22). Such a conformation facilitates the manufacturing and assembling of the inhaler, considerably reducing the costs of the mass production. With reference to FIGS. 7, 8, 9, 10, 11 and 12, the operation of incision of the capsule (5) and the consequent inhalation of the powdered drug by the user, can be easily performed following these operations: it's sufficient to keep the block (B) of the inhaler with one hand and, once the capsule (5) has been placed in the compartment (23) of the cover (21), slightly pressing on the capsule (5), with the thumb of the other hand you'll rotate the cover (21) on the element (22) of block (B), by means of the support (24), so as to split the case of the capsule (5) and open it; then you place the device into your mouth and inhale the powdered drug.

With reference to FIGS. 7, 8, 9, 10, 11 and 12, the capsule (5) is cut by means of a cutting element (27) on the base of the chamber (25) of the element (22) of block (B), which splits the lower part of the case of the capsule (5). The consequent dispersion of the powdered drug contained in the capsule (5) into the chamber (25) is caused by the rotation of the cover (21) on the element (22), performed thanks to the support (24) connected to the cover (21). The rotation of the cover (21) on the element (22) of block (B) causes the split of the case of the capsule (5) so as to let the powdered drug completely come out from the capsule (5).

With reference to FIGS. 7, 8, 9, 10, 11 and 12, the cutting element (27) has a rectangular pointed shape, so as to facilitate the cut of the case of the capsule (5) during the operation of its incision.

With reference to FIGS. 7, 8, 9, 10, 11 and 12, the cutting element (27) is made of plastic or other suitable material ensuring the necessary stiffness, so that it's sufficient a moderate force to split the case of the capsule (5), by slightly pressing on the capsule (5), with the thumb of one's hand.

With reference to FIGS. 7, 8, 9, 10, 11 and 12, in order to ensure a greater dispersion of the powdered drug into the chamber (26), this takes such a conformation that the half-conical shape, with the vertex downwards, facilitates the outflow of the powder towards the mouthpiece (12) so that it can be easily and conveniently inhaled by the user.

With reference to FIGS. 7, 8, 9, 10, 11 and 12, under the compartment (23) where the capsule (5) is placed in order to be cut, there is a chamber (25), with a grid lower surface (9) having a series of slots, which allows the pieces of the case of the capsule (5) to remain inside the chamber (25). Said grid (28) has the important function to prevent the powder from aggregating in a humid atmosphere, obstructing in this way its dispersion into the next chamber (26) and the consequent inhalation by the user.

While a particular form of the invention has been illustrated and described, it will be apparent that various modifications can be made without departing from the spirit and scope of the invention. Thus, although the invention has been described in detail with reference to preferred embodiments, those having ordinary skill in the art appreciate that various modification can be made without departing from the invention.

It is specified that the appearance and the basis conformation of the object described is indicative, other advantages of the device will appear to those skilled in the art from the containing of the appended drawings.

It will be readily appreciated that the forms of the invention described above are intended for purposes of illustration only, and numerous changes in the details of construction and materials employed may be made without departing from the spirit of the invention or the scope of the appended claims.

BRIEF DESCRIPTION OF DRAWINGS

FIGS. 1 and 2 show respectively the frontal and side view of the inhaler in the embodiment where the device is essentially formed by a block, obtained by the assembly of the elements (1) (2) and (3), which are characterized by their coaxial position with the entire system, and by the container (15), inside which the capsules are placed in order to be wholly preserved until the moment of their use. These figures show also the frontal and side view of the long rectangular support (7), by means of which it's possible to rotate the element (2) on the elements (1) and (3) in order to ensure the incision of the capsule.

FIG. 3 shows a side sectional view of the inhaler cut by a vertical plane passing through the diameter of the circular section. This figure clearly distinguishes the block (A) from the container (15), where the capsules (5) are kept until the moment of their use.

The block (A) is formed by the effective assembly of the elements (1) (2) and (3), in order to ensure the perfect join between the same elements, so as to facilitate to the maximum the operation of incision of the capsule (5) that makes the powdered drug come out. This sectional view shows the block (A) of the device in the moment of the incision of the capsule (5), i.e. with the elements (1) (2) and (3) perfectly fitted each other. The cover (1) comprises the compartment (4) that holds the capsule (5) to be cut. The element (2) is movable compared with the cover (1) and with the element (3), so that, thanks to the support (7), it's possible to rotate the element (2) on the other two elements (1) and (3), which permits to cut the capsule (5). Inside the element (3) there are the two chambers (8) and (10): their main task is to ensure the passage of the powdered drug that is come out from the capsule (5), so that it can be taken by the user.

This figure shows also the container (15) where the capsules (5) are placed in order to be wholly preserved until the moment of their use. The capsules (5) are arranged inside the container in three vertical parallel lines, two of which are drawn in this figure. Each vertical line can comprise a maximum number of capsules (5) and is divided from the other by a thin wall (20), in order to ensure a better arrangement of the capsules (5) inside the container (15). The block (A) and the container (15) are divided by a circular surface (19) through which the capsules (5) can be pulled out, one at a time, in the moment of their use.

FIG. 4 shows the exploded view of the block (A) with the three separated elements:
- the cover (1), comprising the compartment (4) of the capsule (5) at its centre. The vertical axis passing through the centre of the compartment (4) corresponds exactly to the vertical axis of the block (A) and of the entire device, being the latter of circular section along its entire length. The capsule (5) is placed into the compartment (4) in order to be split, so that the user can then take the powdered drug it contains;
- the element (2) is movable compared with the elements (1) and (3) of the block (A) thanks to the long rectangular support (7), by means of which it's possible to rotate the element (2) on the elements (1) and (3) in order to ensure the incision of the capsule (5). When the capsule (5) is placed into the compartment (4), the lower part of its case will touch the half-conical opening (6) whose internal side surfaces (6a, 6b) constitute the real cutting system of the capsule (5), as they are made of such a material that makes their surface rough;
- the element (3), principally comprising the chambers (8) and (10), has the main task to ensure the passage of the powdered drug that is come out from the capsule (5), so that it can be taken by the user. In the moment of incision of the capsule (5), the powdered drug starts dispersing into the chamber (8) and then falls for gravity into the chamber (10), divided from the former by means of a grid surface (9) that keeps the case of the capsule (5) and prevents non-powdered drug fragments from aggregating. The half-conical shape of the chamber (10), of variable section along its height, facilitates the dispersion of the powdered drug towards the area next to the mouthpiece (12). Thus, the powdered drug that is found inside the chamber (10) is ready to be inhaled, by placing the mouthpiece (12) into the user's mouth; during this operation, the powdered drug passes through a porous filter (11) that prevents it from aggregating.

The element (3), on its upper part, comprises some components capable of fitting it to the other two elements (1) and (2) of block (A):
- the element (1) is fitted to the element (3) by means of three equal components placed at the vertexes of an equilateral triangle inscribed in the circular section of the upper part of the element (3); each of them is formed by a small wing (13a), placed in horizontal position and belonging to the element (3), which perfectly fits inside the notch (13b) of the element (1);
- the element (2) is fitted to the element (3) by means of two equal components placed in opposite position, in the internal upper part of the element (3); each of them is formed by a small wing (14a), placed in vertical position and belonging to the element (3), which perfectly fits inside the groove (14b) of the element (2).

FIG. 5 shows the top sectional view of the device at the height of a horizontal plane x—x as depicted in FIG. 1. This figure permits to clearly observe the circular perimeter of the element (3) of block (A). It's then possible to observe:
- the top view of the compartment (4) inside which the capsule (5) is placed in order to be split;
- the top view of the element (2) of block (A), with the support (7) at one of its sides, by means of which it's possible to rotate the element (2) on the other elements (1) and (3) of block (A), in order to cut the capsule (5). The dotted line of the circular perimeter of the element (2) clearly marks the rotation of the element (2) on the element (3) in the clockwise direction indicated by the arrows.

FIG. 6 shows the top sectional view of the device at the height of a horizontal plane y—y as depicted in FIGS. 1 and 3. This figure permits to clearly observe the circular perimeter of the container (15) inside which the capsules (5) are placed in order to be wholly preserved until the moment of their use. The capsules (5) are arranged in three vertical parallel lines (16) (17) and (18), and each line can comprise a maximum number of capsules (5).

FIGS. 7 and 8 show respectively the frontal and side view of the inhaler in the embodiment where the device is essentially formed by a block, obtained by the assembly of the elements (21) and (22), which are characterized by their coaxial position with the entire system, and by the container (15), inside which the capsules are placed in order to be wholly preserved until the moment of their use. These figures show also the frontal and side view of the long rectangular support (24), belonging to the element (21), by means of which it's possible to rotate the element (21) on the element (22) in order to ensure the incision of the capsule.

FIG. 9 shows a side sectional view of the inhaler cut by a vertical plane passing through the diameter of the circular section. This figure clearly distinguishes the block (B) from the container (15), where the capsules (5) are kept until the moment of their use.

The block (B) is formed by the effective assembly of the elements (21) and (22), in order to ensure the perfect join between the same elements, so as to facilitate to the maximum the operation of incision of the capsule (5) that makes the powdered drug come out. This sectional view shows the block (B) of the device in the moment of the incision of the capsule (5), i.e. with the elements (21) and (22) perfectly fitted each other. The cover (21) comprises the compartment (23) that holds the capsule (5) to be cut. The cover (21) is movable compared with the element (22), so that, thanks to the support (24), it's possible to rotate the cover (21) on the other element (22), which permits to cut the capsule (5). Inside the element (22) there are the two chambers (25) and (26): their main task is to ensure the passage of the powdered drug that is come out from the capsule (5), so that it can be taken by the user.

This figure shows also the container (15) where the capsules (5) are placed in order to be wholly preserved until the moment of their use. The capsules (5) are arranged in three vertical parallel lines, two of which are drawn in the figure. Each vertical line can comprise a maximum number of capsules (5) and is divided from the other by a thin wall (20), in order to ensure a better arrangement of the capsules (5) inside the container (15).

The block (B) and the container (15) are divided by a circular surface (19) through which the capsules (5) can be pulled out in the moment of their use.

FIG. 10 shows the exploded view of the block (B), with the three separated elements, and the container (15):
- the cover (21), comprising the compartment (23) of the capsule (5). The vertical axis passing through the centre of the compartment (23) does not correspond to the vertical axis of the block (B) and of the entire device, being the latter of circular section along its entire length. Therefore, in this case, the compartment (23) is located laterally compared with the central position of the circular section of the device. The capsule (5) is placed into the compartment (23) in order to be split, so that the user can then take the powdered drug it contains. The cover (21) is movable compared with the other element (22) of block (B) thanks to the long rectangular support (24), by means of which it's possible to rotate the cover (21) on the element (22) in order to ensure the incision of the capsule (5). When the capsule (5) is placed into the compartment (23), the lower part of its case will touch the cutting element (27), consisting of a rectangular pointed blade, which constitutes, in this solution, the real cutting system of the capsule (5).

the element (22), principally comprising the chambers (25) and (26), has the main task to ensure the passage of the powdered drug that is come out from the capsule (5), so that it can be taken by the user. In the moment of incision of the capsule (5), the powdered drug starts dispersing into the chamber (25) and then falls for gravity into the chamber (26), divided from the former by means of a grid surface (28) that keeps the case of the capsule (5) and prevents non-powdered drug fragments from aggregating. The chamber (26) is formed by an upper circular part, of constant section, and by a half-conical lower part, immediately after the first one, of variable section along its height, which facilitates the dispersion of the powdered drug towards the area next to the mouthpiece (12). Thus, the powdered drug that is found inside the chamber (26) is ready to be inhaled, by placing the mouthpiece (12) into the user's mouth; during this operation, the powdered drug passes through a porous filter (11) that prevents it from aggregating.

the container (15) inside which the capsules (5) are placed in order to be wholly preserved until the moment of their use. The capsules (5) are arranged in three vertical parallel lines, two of which are drawn in this figure. Each vertical line can comprise a maximum number of capsules (5) and is divided from the other by a thin wall (20) in order to ensure a better arrangement of the capsules (5) inside the container (15). In this figure it's also possible to observe the last upper part (31) of the container (15) that comprises the half-conical part of variable section of the chamber (26) belonging to the element (22). In particular, the circular wall (32) comprises and perfectly holds the last part of the element (22), consisting of the mouthpiece (12) through which the powdered drug that comes out from the capsule (5) passes, in order to be directly inhaled by the user.

The elements (21) and (22) of block (B) comprise some components capable of fitting each other, and by means of which it's possible to rotate the cover (21) on the element (22), in order to ensure the incision of the capsule (5):

the element (21) is fitted to the element (22) by means of a circular groove along the entire perimeter of the base of the cover (21) and of the upper end of the element (22); with reference to the drawing, it's possible to identify the tracks (29a) and (30a) of the groove on the internal upper part of the element (22), that perfectly fit into the tracks (29b) and (30b) of the groove on the external lower part of the cover (21).

FIG. 11 shows the top sectional view of the device at the height of a horizontal plane k—k as depicted in FIG. 7. This figure permits to clearly observe the circular perimeter of the element (22) of block (B). It's then possible to observe:

the top view of the compartment (23) inside which the capsule (5) is placed in order to be split;

the projection of the cover (21) of block (B), with the support (24) at one of its sides, by means of which it's possible to rotate the cover (21) on the element (22) of block (B), in order to cut the capsule (5).

The dotted line of the circular perimeter of the cover (21) clearly marks the rotation of the cover (21) on the element (22) in the clockwise direction indicated by the arrows.

FIG. 12 shows the top sectional view of the device at the height of a horizontal plane m—m as depicted in FIG. 7. This figure permits to clearly observe the circular perimeter of the container (15) inside which the capsules (5) are placed in order to be wholly preserved until the moment of their use. The capsules (5) are arranged in three vertical parallel lines (16) (17) and (18), and each line can comprise a maximum number of capsules (5). This figure also shows the projection of the support (24), by means of which it's possible to rotate the cover (21) on the element (22).

The present invention provides the following advantages:

A pen-shaped inhaling device for dispersing powdered medicament contained in one or more capsules through the respiratory tract, characterized in that it comprises:

means to preserve the capsules in order to be easily and conveniently carried and used, with a long-shaped container (15) harmoniously integrated in the whole device, which takes such a conformation similar to the one of a pen;

means to hold the capsule and allow the powdered medicament drug it contains to come out, by an assembly of two or more separated elements that constitute a single block (A) or (B), connected to the container of the capsules;

means to hold the capsule inside said block by a compartment (4) (23) into which the capsule is placed and held still during the operation of incision, so as to guarantee the dispersion of the powdered drug into a chamber of said block;

means to split the capsule, by a cutting element preferably formed by a point, a blade, a cutting surface, or any other cutting element capable of perforating or cutting the capsule, integrated in the block (A) (B);

means to cut the capsule and to cause the powdered drug to completely come out from the capsule, with a support (2) (21) by means of which it's possible to rotate one element on the other ones forming the block of the inhaler;

means to hold the pieces of the case of the capsule, after it has been split, and to prevent the powder from aggregating, by a chamber (8) (25) with a grid lower surface (9) (28) that keeps the bigger pieces of the drug not completely pulverized, as well as the pieces of the case of the capsule (5), while letting the powdered drug pass through;

means to deliver the powder of the capsule released into the lower part of the block of the inhaler, by a mouthpiece (12) from which the user can directly inhale the powder;

means to prevent the powder from aggregating, by a porous filter (11) placed near the mouthpiece of the inhaler.

In another advantage dependent upon the first advantage, a pen-shaped Inhaling device is characterized in that the capsule is cut by means of a rough surface touching it. This system comprises:

means to preserve the capsules (5) in order to be easily and conveniently carried and used, with a container (15) harmoniously integrated in the whole device, inside which the capsules (5) are arranged in three vertical parallel lines (16) (17) and (18);

means to hold a capsule (5) inside the block (A), by an element (1) comprising an open compartment (4), into which the capsule (5) is placed, with its side walls touching the perimeter of said compartment (4);

means to cut the capsule (5), by an element (2) comprising a half-conical opening (6), with the vertex upwards and with rough internal side surfaces (6a, 6b) that facilitate the operation of incision of the lower part of the case of the capsule (5), following the rotation of the element (2) on the other elements (1) and (3) of block (A);

means to release the powdered drug inside the block (A), immediately after the case of the capsule (5) has been split, by an element (3) formed by two chambers (8) and (10), divided one from the other by a grid (9);

means to rotate the element (2) on the elements (1) and (3) forming block (A), by a long rectangular support (7) connected to the element (2);

means to fit the element (1) to the element (3) of the block (A), by three equal components placed at the vertexes of an equilateral triangle inscribed in the circular section of the upper part of the element (3) of the block (A); each of them is formed by a small wing (13a), placed in horizontal position and belonging to the element (3), which perfectly fits inside the notch (13b) of the element (1);

means to fit the element (2) to the element (3) of the block (A), by two equal components; each of them is formed by a small wing (14a), placed in vertical position and belonging to the element (3), which perfectly fits inside the groove (14b) of the element (2);

means to hold the pieces of the case of the capsule (5), after it has been split, and to prevent the powder from aggregating, by a chamber (8) with a grid lower surface (9) having a series of slots that keep the bigger pieces of the drug not completely pulverized, as well as the pieces of the case of the capsule (5), while letting the powdered drug pass through;

means to deliver the powder of the capsule (5) released into the chamber (10), by a mouthpiece (12) from which the user can directly inhale the powder.

means to prevent the powder from aggregating, by a porous filter (11) placed near the mouthpiece (12) of the inhaler.

In yet another advantage dependent upon the second advantage above, a pen-shaped inhaling is characterized in that the body of the inhaler is essentially formed by two parts that can be assembled each other: the block (A) and the container (15), inside which the capsules (5) are preserved until the moment of their use. The block (A), in its turn, is essentially formed by three parts that can be assembled each other: the cover (1) and the elements (2) and (3). Such a conformation facilitates the manufacturing and assembling of the inhaler, considerably reducing the costs of the mass production.

In still another advantage of the present invention, dependent upon the second advantage above, a pen-shaped inhaling device is characterized in that the capsule (5) is cut by rubbing the lower part of its case over the rough surface of the half-conical opening (6); the internal surfaces (6a, 6b) of said opening (6) are made of a suitable material composed of a paste of plastic and vitreous material, which makes them sufficiently rough to guarantee the incision of the case of the capsule (5) following the rubbing caused by the rotation of the element (2), by means of the support (7) connected to the same element (2); said material forming the rough internal surfaces of the opening (6) is also sufficiently stiff, so as to prevent their crumbling or any pulverization of their external layer.

In another advantage of the present invention dependent upon the second advantage above, a pen-shaped inhaling device is characterized in that the operation of incision of the capsule (5) and the consequent inhalation of the powdered drug by the user, can be easily performed following these operations: it's sufficient to keep the block (A) of the inhaler with one hand and, once the capsule (5) has been placed in the compartment (4) of the cover (1), with the thumb of the other hand you'll rotate the element (2) on the other elements (1) and (3) forming block (A), by means of the support (7), so as to split the case of the capsule (5); then you place the device into your mouth and inhale the powdered drug.

In another advantage dependent upon the second advantage above, a pen-shaped inhaling device is characterized in that, in order to ensure a greater dispersion of the powdered drug into the chamber (10), this takes such a conformation that the half-conical shape, with the vertex downwards, facilitates the outflow of the powder towards the mouthpiece (12) so that it can be easily and conveniently inhaled by the user.

In another advantage of the present invention dependent upon the first advantage above, a pen-shaped inhaling device is characterized in that the capsule is cut by splitting its case with a cutting element. This system comprises:

means to preserve the capsules (5) in order to be easily and conveniently carried and used, with a container (15) harmoniously integrated in the whole device, inside which the capsules (5) are arranged in three vertical parallel lines (16) (17) and (18);

means to hold a capsule (5) inside the block (B), by an element (21) comprising an open compartment (23), into which the capsule (5) is placed, with its side walls touching the perimeter of said compartment (23);

means to split the capsule (5), by a cutting element (27), consisting of a rectangular pointed blade; when the capsule (5) is placed into the compartment (23), the lower part of its case will be cut for incision by the cutting element (27);

means to release the powdered drug inside the block (B), after the split of the capsule (5), by an element formed by two chambers (25) and (26), divided one from the other by a grid (28);

means to rotate the cover (21) on the element (22) of the block (B), in order to cause the cutting element (27) split the case of the capsule (5) and let the powdered drug completely come out, by a long rectangular support (24) connected to the cover (21);

means to fit the cover (21) to the element (22) of the block (B), by a circular groove along the entire perimeter of the base of the cover (21) and of the upper end of the element (22), since the tracks (29a) and (30a) of the groove on the internal upper part of the element (22), perfectly fit into the tracks (29b) and (30b) of the groove on the external lower part of the cover (21);

means to hold the pieces of the case of the capsule (5), after it has been split, and to prevent the powder from aggregating, by a chamber (25) with a grid lower surface (28) having a series of slots that keep the bigger pieces of the drug not completely pulverized, as well as the pieces of the case of the capsule (5), while letting the powdered drug pass through;

means to deliver the powder of the capsule (5) released into the chamber (26), by a mouthpiece (12) from which the user can directly inhale the powder.

means to prevent the powder from aggregating, by a porous filter (11) placed near the mouthpiece (12) of the inhaler.

In yet another advantage of the present invention, dependent upon the seventh advantage above, a pen-shaped inhaling is characterized in that the body of the inhaler is essentially formed by two parts that can be assembled each other: the block (B) and the container (15), inside which the capsules (5) are placed until the moment of their use. The block (B), in its turn, is essentially formed by two parts that can be assembled each other: the cover (21) and the element (22). Such a conformation facilitates the manufacturing and assembling of the inhaler, considerably reducing the costs of the mass production.

In still another advantage, dependent upon the seventh advantage above, a pen-shaped inhaling device is characterized in that the operation of incision of the capsule (5) and the consequent inhalation of the powdered drug by the user, can be easily performed following these operations: it's sufficient to keep the block (B) of the inhaler with one hand and, once the capsule (5) has been placed in the compartment (23) of the cover (21), slightly pressing on the capsule (5), with the thumb of the other hand you'll rotate the cover (21) on the element (22) of the block (B), by means of the support (24), so as to split the case of the capsule (5) and open it; then you place the device into your mouth and inhale the powdered drug.

In another advantage dependent upon the seventh advantage above, a pen-shaped inhaling device is characterized in that the capsule (5) is cut by means of a cutting element (27) on the base of the chamber (25) of the element (22) of the block (B), which splits the lower part of the case of the capsule (5). The consequent dispersion of the powdered drug contained in the capsule (5) into the chamber (25) is caused by the rotation of the cover (21) on the element (22), performed thanks to the support (24) connected to the cover (21). The rotation of the cover (21) on the element (22) of the block (B) causes the split of the case of the capsule (5) so as to let the powdered drug completely come out from the capsule (5).

In another advantage of the invention, dependent upon the seventh advantage described above, a pen-shaped inhaling device is characterized in that the cutting element (27) has a rectangular pointed shape, so as to facilitate the cut of the case of the capsule (5) during the operation of its incision.

In another advantage of the present invention, dependent upon the seventh advantage described above, a pen-shaped inhaling is characterized in that the cutting element (27) is made of plastic or other suitable material ensuring the necessary stiffness, so that it's sufficient a moderate force to split the case of the capsule (5), by slightly pressing on the capsule (5), with the thumb of one's hand.

In another advantage of the invention, dependent upon the seventh advantage described above, a pen-shaped inhaling device is characterized in that, in order to ensure a greater dispersion of the powdered drug into the chamber (26), this takes such a conformation that the half-conical shape, with the vertex downwards, facilitates the outflow of the powder towards the mouthpiece (12) so that it can be easily and conveniently inhaled by the user.

In still another advantage of the present invention, dependent upon the advantages described above, a pen-shaped is characterized in that it takes such a shape similar to the conformation of a normal cylindrical pen or pencil, with the vertical dimension greater than the other two, however comparable with the dimensions of a normal pen.

In another advantage, dependent upon the advantages described above, a pen-shaped inhaling device is characterized in that the external support (7) or (24) facilitates the convenient transport of the inhaler (for example in the pocket of your shirt) thanks to its clip.

In still another advantage, dependent upon the advantages described above, a pen-shaped inhaling device is characterized in that it may be used more times and, in order to ensure the greatest hygiene, the mouthpiece (12) from which the user inhales the powdered drug that is come out from the capsule (5), is held and protected by the upper part of the container (15), so that, when the inhaler is not used, the maximum protection from the dust and, in general, from external agents will be guaranteed.

In another advantage of the present invention, dependent upon the advantages described above, a pen-shaped inhaling device is characterized in that the compartment (4) or (23), into which the capsule (5) is placed in order to be cut, has such a size that permits the complete insertion of the capsule (5) inside it, ensuring a greater stability of the same capsule (5) during the operation of its incision, and preventing it from accidentally escaping from said compartment (4) or (23).

In another advantage, dependent upon the advantages described above, a pen-shaped inhaling device is characterized in that the powder released on the base of the device is inhaled by the user, placing directly the mouthpiece (12) into his/her mouth and breathing in, so that the powdered drug coming out from the mouthpiece (12) enters the mouth and reaches the lungs.

I claim:

1. A pen-shaped inhaling device for dispersing powdered medicament contained in one or more capsules through the respiratory tract, comprising:
   means for storing one or more capsules in order to conveniently carry and use said device and to allow the powdered medicament within said capsules to exit, each said one or more capsules enclosed in an outer case, wherein said means for storing one or more capsules comprises a substantially pen shaped elongated container integrated with the inhaling device, and an assembly having an upper portion, a central portion, and a lower portion that are integrated to produce a single integrated block, said block connected to the elongated container;
   means for maintaining said one or more capsules within said block comprising a compartment into which the one or more capsules are placed and are held during incision of the capsules, so as to guarantee proper dispersion of the powdered medicament into said block; means for splitting said one or more capsules;
   means for capturing pieces of the case of the capsules after said capsules have been split and to prevent the powdered medicament from aggregating; and
   means for delivering the powdered medicament of the capsules released into the lower portion of the block of the inhaling device, said means for delivering comprising a mouthpiece from which a user can directly inhale the powdered medicament.

2. The pen-shaped inhaling device according to claim 1, wherein said means for splitting said one or more capsules comprises a cutting element formed by a pointed end portion or other cutting element capable of perforating or cutting said capsules, said cutting element integrated into said block, said cutting element having supporting means to allow for the rotation of portion of said block upon a second portion of said block.

3. The pen-shaped inhaling device of claim 1 wherein said means for capturing pieces of the case of the capsules after said capsule has been split and to prevent the powdered medicament from aggregating comprises a lower grid surface that traps larger pieces of the powdered medicament not completely pulverized, as well as pieces of the case of the capsules, while allowing pulverized powdered medicament to pass through.

4. The pen-shaped inhaling device according to claim 1, wherein said means for preventing the powdered medicament from aggregating comprising a porous filter placed near the mouthpiece of the inhaling device.

5. A pen-shaped inhaling device for dispersing powdered medicament contained in one or more capsules through the respiratory tract, wherein each capsule is cut by means of a rough surface coming in contact with each said capsule, said inhaling device comprising:

means for storing said one or more capsules in order to conveniently carry and use said device, each said one or more capsules enclosed in an outer case, said means for storing said one or more capsules comprising a substantially pen shaped elongated container integrated with the inhaling device, inside of which said one or more capsules are arranged in a plurality of substantially vertical parallel rows, and a block connected to the elongated container;

means for holding said one or more capsules inside said elongated container, said holding means comprising an open compartment into which the one or more capsules are placed, with the side walls of said capsules touching the perimeter of said compartment;

means for cutting the capsules;

means for releasing the powdered medicament inside the block immediately after the case of the capsules have been split;

means for holding the pieces of the case of the capsule after it has been split, and for preventing the powdered medicament from aggregating; and means for delivering the powdered medicament of the capsule released into the block, said means for delivering the powdered medicament of the capsule comprising a mouthpiece from which a user can directly inhale the powdered medicament.

6. The pen-shaped inhaling device according to claim 5, wherein said block is comprised of an upper portion, a central portion, and a lower portion that are integrated to produce a single integrated block, said lower portion comprised of an upper chamber and a lower chamber.

7. The pen-shaped inhaling device according to claim 6 further comprising means for rotating said middle portion of said block upon said upper and lower portions of said block.

8. The pen-shaped inhaling device according to claim 7, wherein said means for rotating said middle portion of said block upon said upper and lower portions of said block comprises an elongated rectangular support member connected to said middle portion of said block.

9. The pen-shaped inhaling device according to claim 8, wherein said means for cutting said capsules comprises a cutting element with a half-conical opening therethrough, said half-conical opening having an internal cutting surface around its inner perimeter to facilitate operation of incision of a lower part of the case of each said capsule following said rotation of said middle portion upon said upper and lower portions of said block.

10. The pen-shaped inhaling device according to claim 9, wherein said capsule is cut by rubbing a lower part of the case of said capsule over said internal cutting surface around said half-conical opening wherein said internal cutting surface of said opening is made of a material which makes said internal cutting surface sufficiently rough to guarantee incision of the case of the capsule, said rubbing caused by rotation of said elongated support member.

11. The pen-shaped inhaling device according to claim 10, wherein said suitable material is comprised of a paste of plastic and vitreous material, said material forming said internal rough cutting surface of the opening, said material is sufficiently stiff so as to prevent crumbling or any pulverization of the material's external layer.

12. The pen-shaped inhaling device according to claim 9, wherein the operation of incision of the capsule and consequent inhalation of the powdered medicament can be easily performed by the user holding said block of the inhaling device with one hand, and, once the capsule has been placed in said compartment, rotating said middle portion upon said lower and upper portions by means of said elongated support member so as to split the case of the capsule.

13. The pen-shaped inhaling device according to claim 9, wherein, in order to ensure a greater dispersion of the powdered medicament into the lower chamber, said cutting element having said half conical shape is positioned facing downwards, thereby facilitating the outflow of the powdered medicament towards the mouthpiece so that the powdered medicament can be easily and conveniently inhaled by the user.

14. The pen-shaped inhaling device according to claim 6, wherein said means for holding pieces of the case of the capsule after it has been split, and for preventing the powdered medicament from aggregating, comprises a grid member located within said lower portion of said block, said grid member having a series of slots that trap larger aggregated pieces of the powdered medicament not completely pulverized, as well as the pieces of the case of the capsule, while allowing non-aggregated powdered medicament to pass through.

15. The pen-shaped inhaling device according to claim 6, further comprising means for fitting the upper portion of said block to said lower portion of said block.

16. The pen-shaped inhaling device according to claim 15, wherein said means for fitting the upper portion of said block to said lower portion of said block comprises a plurality of protrusions extending upwards from the top of said upper portion of said block, and a plurality of corresponding notches situated at the bottom of said upper portion of said block, wherein each said notch receives a corresponding said protrusion.

17. The pen-shaped inhaling device according to claim 6, further comprising means for fitting the middle portion of said block to said lower portion of said block.

18. The pen-shaped inhaling device according to claim 17, wherein said means for fitting the middle portion of said block to said lower portion of said block comprises a plurality of upwardly extending wing elements extending from the top of said upper portion of said block, and a plurality of corresponding grooves situated at the bottom of said middle portion of said block, wherein each said groove receives a corresponding said wing element.

19. The pen-shaped inhaling device according to claim 6, further comprising a porous filter placed near the mouthpiece of the inhaler to prevent the powdered medicament from aggregating.

20. The pen-shaped inhaling device according to claim 6, wherein said upper portion of said block acts as a cover of said inhaling device thereby facilitating manufacturing and assembling of the inhaling device, and considerably reducing the costs of mass production.

21. A pen-shaped inhaling device for dispersing powdered medicament contained in one or more capsules through the respiratory tract, said inhaling device comprising:

means for preserving said one or more capsules in order to be easily and conveniently carried and used, said capsules enclosed within an outer case, said means for preserving comprising a container integrated in the inhaling device, inside which the capsules are arranged in a plurality of substantially vertical parallel lines;

means for holding the capsule to be cut inside a block comprising a cover having an open compartment into which the capsule to be cut is placed;

means for splitting the capsule comprising a cutting element having a pointed blade, whereby when the capsule is placed into the compartment, a lower part of its case will be cut by the cutting element;

means for releasing the powdered medicaments inside the block after the splitting of the capsule, said releasing means comprising a middle element having an upper chamber and a lower chamber, said upper and said lower chamber separated from each other by a grid member;

means to rotate the cover upon the middle element of the block in order to cause the cutting element to split the case of the capsule being cut and allow the powdered medicament to exit, said cover rotating means comprising an elongated rectangular support member connected to the cover;

means for holding pieces of the case of the capsule after it has been split and for preventing the powdered medicament from aggregating, said means for holding pieces of the case comprising said grid member including a series of slots that trap larger pieces of the powdered medicament not completely pulverized as well as the pieces of the case of the capsule, while allowing non-aggregated powdered medicament to pass through; and means for delivering the powdered medicament released into the lower chamber, comprising a mouthpiece from which a user can directly inhale the powdered medicament.

22. The pen-shaped inhaling device according to claim 21 wherein said means for preventing the powdered medicament from aggregating comprising a porous filter element placed near the mouthpiece of the inhaling device.

23. The pen-shaped inhaling device according to claim 21 further comprising means for mounting the cover to the middle element of the block, said mounting means comprising a circular groove along the perimeter of a base of the cover and of an upper end of the middle element, such that tracks along the groove of the perimeter of the base of the cover fit into corresponding tracks of a groove on the external lower part of the cover.

24. The pen-shaped inhaling device according to claim 21, wherein the inhaling device is essentially formed of a body, said body comprised of said block and said container, inside of which the capsules are placed until their use, said block formed from the cover and the middle element, such formation facilitating the manufacturing and assembling of the inhaling device, thereby considerably reducing costs of mass production of said inhaling device.

25. The pen-shaped inhaling device according to claim 21, wherein operation of incision of the capsule and consequent inhalation of the powdered medicament can be easily performed by the user holding said block of the inhaling device with one hand, and, once the capsule has been placed in said compartment, rotating said cover upon said middle element by means of said elongated support member so as to split the case of the capsule.

26. The pen-shaped inhaling device according to claim 21, wherein the capsule is cut by means of rotation of the cover upon the middle element due to the elongated support member, said cutting element splitting a lower part of the case of the capsule thereby dispersing the powdered medicament contained in the capsule into the upper chamber.

27. The pen-shaped inhaling device according to claim 21, the cutting element is made of plastic or other material ensuring the necessary stiffness, such that a sufficiently moderate force can split the case of the capsule, upon slight pressure on the capsule.

28. The pen-shaped inhaling device according to claim 21, wherein, in order to ensure a greater dispersion of the powdered medicament into the lower chamber, said cutting element having said half conical shape is positioned facing downwards, thereby facilitating the outflow of the powdered medicament towards the mouthpiece so that the powdered medicament can be easily and conveniently inhaled by the user.

29. The pen-shaped inhaling device according to claim 21 wherein said inhaling device forms a shape similar to that of a cylindrical pen or pencil.

30. The pen-shaped inhaling device according to claim 21, wherein said elongated support member facilitates convenient transport of the inhaling device, said elongated member adapted to clip on to an article of clothing or on an object.

31. The pen-shaped inhaling device according to claim 21, wherein said mouthpiece from which the user inhales the powdered medicament that exits the capsule is held and protected by an upper part of the container, such that, when the inhaling device is not in use, maximum protection from the dust and external agents is provided to ensure maximum hygiene.

32. The pen-shaped inhaling device according to claim 21, wherein the compartment into which the capsule is placed in order to be cut has such a size that permits complete insertion of the capsule therein, thereby ensuring a greater stability of the capsule during the operation of its incision, and preventing said capsule from accidentally escaping from said compartment.

33. The pen-shaped inhaling device according to claim 21 wherein the powdered medicament released by the device is directed into the mouthpiece so that the powdered medicament coming out from the mouthpiece enters the mouth and reaches the lungs of the user.

* * * * *